US009920352B2

(12) United States Patent
Mutz et al.

(10) Patent No.: US 9,920,352 B2
(45) Date of Patent: Mar. 20, 2018

(54) ACOUSTIC RADIATION FOR EJECTING AND MONITORING PATHOGENIC FLUIDS

(71) Applicant: Labcyte Inc., San Jose, CA (US)

(72) Inventors: Mitchell W. Mutz, La Jolla, CA (US); Richard N. Ellson, Palo Alto, CA (US)

(73) Assignee: Labcyte Inc., San Jose, CA (US)

( * ) Notice: Subject to any disclaimer, the term of this patent is extended or adjusted under 35 U.S.C. 154(b) by 0 days.

(21) Appl. No.: 13/858,832

(22) Filed: Apr. 8, 2013

(65) Prior Publication Data

US 2013/0224731 A1    Aug. 29, 2013

Related U.S. Application Data

(62) Division of application No. 12/174,824, filed on Jul. 17, 2008, now abandoned, which is a division of application No. 10/199,907, filed on Jul. 18, 2002, now Pat. No. 7,405,072.

(51) Int. Cl.

| C12Q 1/22 | (2006.01) |
|---|---|
| B01L 3/02 | (2006.01) |
| B01L 3/00 | (2006.01) |
| C40B 40/06 | (2006.01) |
| C40B 40/10 | (2006.01) |
| C40B 60/14 | (2006.01) |

(52) U.S. Cl.
CPC .............. *C12Q 1/22* (2013.01); *B01L 3/0268* (2013.01); *B01L 3/0293* (2013.01); *B01J 2219/00362* (2013.01); *B01J 2219/00378* (2013.01); *B01J 2219/00659* (2013.01); *B01J 2219/00722* (2013.01); *B01J 2219/00725* (2013.01); *B01L 3/508* (2013.01); *B01L 2200/0647* (2013.01); *B01L 2400/0436* (2013.01); *C40B 40/06* (2013.01); *C40B 40/10* (2013.01); *C40B 60/14* (2013.01)

(58) Field of Classification Search
None
See application file for complete search history.

(56) References Cited

U.S. PATENT DOCUMENTS

| 3,774,717 | A | * | 11/1973 | Chodorow | ........... G01N 29/032 |
|---|---|---|---|---|---|
| | | | | | 340/621 |
| 4,212,190 | A | * | 7/1980 | Coover et al. | ................ 73/24.03 |
| 4,308,547 | A | | 12/1981 | Lovelady et al. | |
| 5,507,178 | A | | 4/1996 | Dam et al. | |
| 5,520,715 | A | | 5/1996 | Oeftering et al. | |
| 5,608,164 | A | * | 3/1997 | MacLauchlan | ....... G01F 23/284 |
| | | | | | 73/290 V |
| 5,722,479 | A | | 3/1998 | Oeftering et al. | |
| 5,798,779 | A | | 8/1998 | Nakayasu et al. | |
| 5,869,748 | A | * | 2/1999 | Stevenson et al. | .......... 73/53.01 |
| 5,880,364 | A | | 3/1999 | Dam et al. | |
| 5,895,680 | A | * | 4/1999 | Cirigliano | ................ A23D 7/06 |
| | | | | | 426/321 |
| 6,022,742 | A | | 2/2000 | Kopf et al. | |
| 6,326,213 | B1 | * | 12/2001 | Letcher et al. | ............... 436/518 |
| 6,938,995 | B2 | | 9/2005 | Mutz et al. | |
| 2002/0037375 | A1 | | 3/2002 | Ellson et al. | |
| 2002/0037579 | A1 | | 3/2002 | Ellson et al. | |
| 2002/0064808 | A1 | | 5/2002 | Mutz et al. | |
| 2002/0064809 | A1 | | 5/2002 | Mutz et al. | |
| 2002/0090720 | A1 | | 7/2002 | Mutz et al. | |
| 2002/0125424 | A1 | | 9/2002 | Ellson et al. | |
| 2002/0142286 | A1 | | 10/2002 | Mutz et al. | |
| 2002/0171037 | A1 | | 11/2002 | Ellson et al. | |
| 2003/0101819 | A1 | | 6/2003 | Mutz et al. | |
| 2004/0025576 | A1 | * | 2/2004 | Glauser et al. | ............... 73/61.79 |

FOREIGN PATENT DOCUMENTS

WO    WO 0025125 A1 *    5/2000    .............. B01F 11/02

OTHER PUBLICATIONS

Backer et al. 1996 (Effect of Heat on the sterilization of artificially contaminated water; J Travel Med; 3:1-4).*
Camper et al. 1991 (Growth kinetics of coliform bacteria under conditions relevant to drinking water distribution systems; Applied and Environmental Microbiology; 57(8):2233-2239.*
Farrell et al. 1967 (Temperature Effects on Microorganisms; Annu. Rev. Microbiol. 21:101-120).*
Miyamura et al. 1975 (Growth Characteristics of Acute Hemorrhagic Conjunctivitis (AHC) Virus in Monkey Kidney Cells; Intervirology 4: 279-286).*
Amemiya et al., "Ink Jet Printing with Focused Ultrasonic Beams," Proceedings of the 1997 IS&T NIP13 International Conference on Digital Printing Technologies, pp. 698-702 (1997).

* cited by examiner

*Primary Examiner* — Mary Lyons
(74) *Attorney, Agent, or Firm* — Jones Day (57) ABSTRACT

Method and system for monitoring for a change in the amount and/or concentration of a pathogen in a pathogenic fluid. The method includes providing a pathogen-impermeable enclosure enclosing the pathogenic fluid, wherein the pathogenic fluid includes a pathogen and a carrier fluid. Additionally, the method includes acoustically monitoring for a change in the amount and/or concentration of the pathogen enclosed in the pathogen-impermeable enclosure. The acoustically monitoring for a change in the amount and/or concentration of the pathogen enclosed in the pathogen-impermeable enclosure includes generating acoustic radiation directed towards the pathogen-impermeable enclosure, transmitting the acoustic radiation through the pathogen-impermeable enclosure or reflecting the acoustic radiation by the pathogenic fluid, receiving the acoustic radiation transmitted through the pathogen-impermeable enclosure or receiving the acoustic radiation reflected by the pathogenic fluid, and analyzing the received acoustic radiation.

18 Claims, 3 Drawing Sheets

ACOUSTIC RADIATION FOR EJECTING AND MONITORING PATHOGENIC FLUIDS

CROSS-REFERENCE TO RELATED APPLICATIONS

This application is a divisional of U.S. patent application Ser. No. 12/174,824, filed Jul. 17, 2008, abandoned, which is a divisional of U.S. patent application Ser. No. 10/199,907, filed Jul. 18, 2002, now U.S. Pat. No. 7,405,072, both applications being hereby incorporated by reference in their entirety.

TECHNICAL FIELD

The invention relates generally to the use of acoustic radiation in conjunction with pathogenic fluids. In particular, the invention relates to the acoustic monitoring of the pathogenic contents within a reservoir, as well as to the acoustic ejection of pathogenic fluid droplets. The invention also relates to the use of acoustic radiation in conjunction with pathogen-impermeable enclosures.

BACKGROUND

Cultures containing cellular matter may be employed to study pathogenic material such as bacteria and viruses. For example, pathogen-impermeable containers having an interior surface coated with a layer of solid or semisolid medium within which cells are grown may be inoculated with the desired type of cells. After the cells are subjected to conditions appropriate for cultivation, they may be removed from the containers as a suspension and may optionally be concentrated. Also, if desired, viral matter may be extracted from the cells after removal from the containers.

Pathogenic substances, however, including viruses (such as the human immunodeficiency virus (HIV), rabies, and herpes) and bacteria (such as *bacillus anthracis, yersinia pestis*, and those of the *streptococcus* genus), must be handled with extreme care to prevent release of the pathogen. In addition, there exists a need in pharmaceutical, biotechnological, and other scientific industries to quickly screen, identify, and/or process large numbers or varieties of fluids, pathogenic or otherwise. As a result, much attention has been focused on developing efficient, precise, and accurate fluid handling methods that may be used, for example, to carry out screening assays and/or combinatorial techniques. Since fluids used in pharmaceutical, biotechnological, and other scientific industries may be rare and/or expensive, techniques capable of handling small volumes of fluids provide readily apparent advantages over those requiring relatively larger volumes. Furthermore, as pathogenic fluids represent a potential safety hazard, it is also desirable to reduce the quantities used to carry out studies or investigations involving such substances.

Typically, fluids for use in combinatorial methods are provided as a collection or library of organic and/or biological compounds. In many instances, such libraries and collections are provided in a well plate format for screening and/or processing. Well plates are typically single-piece in construction and comprise a plurality of identical wells, wherein each well is adapted to contain a small volume of fluid. Such well plates are commercially available in standardized formats and sizes, and may contain, for example, 96, 384, 1536, or 3456 wells per well plate. Fluids are typically transferred from such well plates, e.g., during formatting and reformatting procedures, using devices that require contact between the fluid to be transferred and a solid surface of a device. For example, capillaries (Eppendorf-type or otherwise) having small interior channels are commonly employed for sample fluid handling by submerging their ends into a pool of sample. Pipetting systems, whether automated, robotic, or otherwise, that have submergible tips may be employed as well. Contact between the solid surface and the fluid to be transferred typically results in surface wetting that represents a source of unavoidable fluid waste as well as a source of potential pathogenic contamination. In addition, if more than one fluid is to contact an interior or exterior solid surface of a non-disposable capillary or pipette tip, the surface must be washed between sample transfers in order to eliminate cross contamination and sample carryover. The liquid biohazard waste created from this wash process must then be disposed of and rendered harmless. It would be desirable to avoid liquid waste generation from repeated wash processes and eliminate additional storage and disposal costs. Disposable pipette tips or capillaries may be used to avoid the generation of liquid waste. However, disposal of solid waste also incurs storage and disposal costs.

Thus, there is a need for fluid handling systems that enable safe and convenient handling, formatting, and reformatting of potentially dangerous bacterial, viral, and other pathogenic specimens. Such fluid handling systems may be used, for example, to perform clinical diagnostic tests, engage in high-throughput drug screening, and carry out growth inhibition studies. In order to ensure that pathogens are not released during fluid handling procedures, pathogen-impermeable enclosures such as glove boxes may be used to contain the pathogenic specimens. Small volume pathogenic cultures, however, often require complicated manual manipulations, which are not easily carried out using glove boxes; thus, performing such procedures in a glove box would likely introduce error during handling and result in possible unwarranted experimental conclusions. Various automated devices to control fluid transfer in closed systems for culturing living pathogens have been developed. U.S. Pat. No. 6,022,742 to Kopf, for example, describes one such automated device.

The use of acoustic energy in printing technology is also known. For example, U.S. Pat. No. 4,308,547 to Lovelady et al. describes a liquid drop emitter that utilizes acoustic principles to eject liquid from a body of liquid onto a moving document in order to form characters or barcodes thereon. Lovelady et al. is directed to a nozzleless inkjet printing apparatus, wherein controlled drops of ink are propelled by an acoustical force produced by a curved transducer at or below the surface of the ink. In contrast to capillaries, syringes, pipettes, inkjet print heads, and other such fluid dispensing devices that employ a nozzle, tip, or tubing for fluid transfer, nozzleless fluid ejection devices as described in the aforementioned patent do not contain components requiring cleaning and/or disposal after use. In addition, disadvantages associated with nozzles or tips in fluid dispensing systems, including clogging, misdirected fluid, improperly sized droplet formation, and the like, are avoided. More recently, acoustic ejection has been employed in contexts other than in ink printing applications. For example, U.S. Patent Application Publication No. 20020037579 to Ellson et al. describes the use of focused acoustic radiation to dispense fluids with sufficient accuracy and precision to prepare biomolecular arrays from a plurality of reservoirs.

Acoustic radiation has also been used to assess the contents of a container adapted to contain a liquid. Traditionally, the contents may be assessed by contacting a sensor with the liquid (see U.S. Pat. No. 5,507,178 to Dam), or by transmitting acoustic radiation through an open top of a container and detecting radiation reflected from an air-liquid interface of the container back to the sensor (see U.S. Pat. No. 5,880,364 to Dam). More recently, U.S. patent application Ser. No. 10/010,972, Publication No. 20030101819, "Acoustic Assessment of Fluids in a Plurality of Reservoirs," inventors Mutz, Ellson, and Foote, filed on Dec. 4, 2001, describes an improved acoustic assessment technique that involves the transmission of acoustic radiation through a reservoir to assess the fluid contents within the reservoir without requiring direct contact with the fluid contents therein. By analyzing a characteristic of the acoustic radiation transmitted through the fluid, various properties of the fluid within the reservoir may be determined. This type of acoustic monitoring may be used advantageously in conjunction with optically opaque reservoirs.

Similarly, focused acoustic energy recently has been used in applications involving biological matter such as living cells. For example, a number of U.S. patent applications describe the use of focused acoustic radiation to manipulate and sort cells. See U.S. Patent Application Publication No. 20020064808 to Mutz et al.; U.S. patent application Ser. No. 09/999,166, Publication No. 20020142286, filed Nov. 29, 2001, for "Focused Acoustic Energy for Ejection Cells from a Fluid," inventors Mutz and Ellson, assigned to Picoliter, Inc. (Mountain View, Calif.); U.S. Patent Application Publication No. 20020064809 to Mutz et al.; and U.S. patent application Ser. No. 10/040,926, Publication No. 20020090720, filed Dec. 28, 2001, for "Focused Acoustic Ejection Cell Sorting System and Method," inventors Mutz, Ellson, and Lee, assigned to Picoliter, Inc. (Mountain View Calif.). Furthermore, the use of focused acoustic radiation has been described for preparing and analyzing a cellular sample surface. (See U.S. patent application Ser. No. 10/087,372, Publication No. 20020171037, filed Mar. 1, 2002, entitled "Method and System Using Acoustic Ejection for Preparing and Analyzing a Cellular Sample Surface," inventors Ellson, Mutz, and Caprioli.)

The use of focused acoustic energy in the context of applications involving pathogenic fluids, however, has previously been unknown in the art. Thus, through the use of focused acoustic radiation, the invention provides previously unrealized opportunities in pathogenic studies.

SUMMARY OF THE INVENTION

In a first embodiment, the invention relates to a method for dispensing one or more droplets of a fluid containing a pathogen. The method involves providing the pathogen-containing fluid in a reservoir and applying focused radiation to the pathogen-containing fluid in the reservoir in a manner effective to eject a droplet of the fluid therefrom. Typically, focused acoustic radiation is employed to carry out the invention. In addition, the invention may be used in conjunction with any of a number of different types of pathogens. The pathogen may be a toxin, virus, and/or bacterium.

In some instances, the pathogen-containing fluid may be comprised of a carrier fluid and a plurality of discrete pathogenic particles. In addition, a plurality of discrete nonpathogenic particles may be present in the carrier fluid as well. Accordingly, the inventive method may involve locating a discrete pathogenic particle in the carrier fluid using focused radiation. When focused acoustic radiation is employed, the location of the pathogenic particle may be detected by virtue of one or more acoustic properties, such as acoustic impedance, which ensures that the ejected droplet contains the pathogenic particle. In some cases, however, the invention may be used to eject droplets containing nonpathogenic particles or no particles at all.

Thus, the invention also provides a method for selecting a localized volume in a pathogenic fluid for removal from a reservoir. When a pathogen-containing fluid is provided in a reservoir and is comprised of a plurality of particles and a carrier fluid, the localized volume may be acoustically located and optionally removed. The localized volume may contain zero, one, or more particles. Furthermore, the localized volume may or may not be pathogenic. In other words, the invention may be used to sort pathogenic from nonpathogenic fluids and particles and vice versa.

The invention may be used to deposit a droplet of fluid on a designated site of a substrate surface, typically by positioning the substrate so that the designated site is in droplet-receiving relationship with respect to the reservoir. In some instances, additional droplets of fluid are deposited on the substrate surface from the same reservoir, or from different reservoirs. When the invention provides a plurality of reservoirs, each reservoir typically contains a different fluid. In any case, droplets may be deposited on the substrate surface at the same site or at different designated sites. When the droplets are deposited at different designated sites, the sites may form an array of sites.

Thus, in some instances, the method may be used to determine whether the pathogen-containing fluid droplet interacts with a compound of interest. This may be carried out by either ensuring that a compound of interest is present at the designated site prior to the deposition of the droplet, or by depositing a compound of interest at the designated site after the deposition of the droplet. The compound of interest, for example, may be deposited on the designated site using focused radiation as well.

Once deposited, a droplet on the substrate surface may be isolated in a pathogen-impermeable enclosure. When a plurality of droplets is deposited, the droplets may be either individually isolated in a plurality of enclosures, or collectively isolated in the same enclosure. In either case, the pathogen-impermeable enclosure or enclosures may be formed by placing a pathogen-impermeable cover in sealing contact with the substrate.

In another embodiment, the invention relates to a method for sealing a fluid in a pathogen-impermeable enclosure. The method involves first providing the fluid in a reservoir and positioning a substrate so that a designated site on a surface thereof is in droplet-receiving relationship with respect to the reservoir. Then, focused radiation is applied to the fluid in the reservoir in a manner effective to eject a droplet of the fluid therefrom onto the substrate surface at the designated site. The fluid droplet at the designated site is then sealed in the pathogen-impermeable enclosure. As before, this method typically employs focused acoustic radiation.

The enclosure is typically sealed after introducing a pathogenic fluid therein, to ensure that the pathogen is not released. The pathogenic fluid droplet may be ejected from the reservoir or dispensed from elsewhere. Thus, the pathogenic fluid droplet may be deposited at the designated site before, during, or after focused radiation is applied to the reservoir to eject a droplet of fluid therefrom. In some instances, however, the enclosure is sealed to ensure that no pathogen is introduced therein. That is, the pathogen may be controllably sealed in or sealed out of the enclosure. In either case, the pathogen-impermeable enclosure is typically opened so as to expose the designated site within the enclosure to the reservoir, and sealed after a fluid droplet has been placed in the enclosure. In some instances, the pathogen-impermeable enclosure may be formed from a cover and the substrate. In such a case, sealing the enclosure may involve placing the cover and the substrate in sealing contact with each other.

Often, droplets from the reservoir are deposited on the substrate surface. In some instances, however, a plurality of reservoirs each containing a different fluid is provided and a droplet from each reservoir is deposited on the substrate surface. In some instances, droplets are deposited at the same designated site. In other instances, the droplets are deposited at different designated sites. The different designated sites may form an array of sites. When fluid droplets are deposited at different designated sites, the droplets may all be sealed in a pathogen-impermeable enclosure, either together in the same compartment, or isolated in separate compartments of the pathogen-impermeable enclosure.

In a further embodiment, the invention provides a device for dispensing one or more droplets of fluid. The device includes a reservoir adapted to contain a fluid, an ejector for applying focused radiation to the reservoir in a manner effective to eject a droplet of fluid from the reservoir, a means for positioning a substrate to receive a droplet of fluid from the reservoir, and a pathogen-impermeable enclosure for isolating the reservoir and substrate therein. Typically, the ejector is an acoustic ejector. Although ordinary inkjet technologies may be employed, it is preferred that the ejector is a nozzleless acoustic device that employs an acoustic generator and a focusing means for focusing the acoustic radiation generated thereby.

The inventive device may include additional features that serve to enhance the performance of the device. For example, the device may further include a means for manually manipulating items within the enclosure without compromising the pathogenic impermeability of the enclosure. In addition, a locating means may be provided for locating a discrete particle in the pathogenic fluid. When the device includes an acoustic generator, the locating means may include an analyzer for analyzing acoustic radiation generated by the acoustic generator. Such an analyzer is typically positioned to receive acoustic radiation generated by the acoustic generator and transmitted through fluid contained in the reservoir. In some instances, the analyzer is positioned to receive acoustic radiation reflected by a free fluid surface contained in the reservoir. In such a case, the analyzer may include a component common to the acoustic generator, e.g., a piezoelectric element.

Typically, the reservoir is detachable from the device and may be adapted for single use. In addition, the device may further include a pathogen-impermeable cover. Such a cover may be adapted to make sealing contact with the reservoir in order to contain a pathogenic fluid therein.

Optionally, the device includes a plurality of reservoirs. In some instances, the reservoirs are provided in a single-piece unit, such as when the reservoirs represent wells of a well plate. The reservoirs are preferably substantially acoustically indistinguishable from each other. In addition, the device may further include a means for successively positioning the acoustic device in an acoustically coupled relationship with each of the reservoirs.

In still another embodiment, the invention relates to a method for monitoring a change in the amount and/or concentration of a pathogen in a pathogenic fluid. The method involves providing a pathogen-impermeable enclosure that encloses a pathogenic fluid comprising a pathogen and a carrier fluid, and acoustically monitoring for a change in the amount and/or concentration of the pathogen enclosed in the pathogen-impermeable enclosure. The method may be used to measure either an increase or a decrease in pathogen content. Thus, the method is particularly suited for carrying out processes and/or assays in which pathogen content and/or concentration is altered. For example, additional material, e.g., nutrients in a culturing solution, may be introduced into the enclosure, which then may be subjected to a temperature change. The temperature may be selected to facilitate an increase or decrease in the amount and/or concentration of the pathogen in the enclosure.

In a further embodiment, the invention relates to a method for detecting for an interaction between a fluid and a compound. The method involves: (a) providing a reservoir containing the fluid; (b) depositing the compound onto a designated site on a surface of a substrate; (c) positioning the substrate so that the designated site is in droplet-receiving relationship with respect to the reservoir; (d) applying focused radiation to the fluid in the reservoir in a manner effective to eject a droplet of the fluid therefrom onto the substrate surface at the designated site; (e) sealing the fluid droplet and the compound at the designated site in a pathogen-impermeable enclosure; and (f) detecting for an interaction between the fluid and the compound. Either the compound, fluid, or both may be pathogenic. The interaction may be detected through various means such as acoustic, optic, fluorescence, magnetic and/or electrical means.

BRIEF DESCRIPTION OF THE DRAWINGS

FIGS. 1A-1D, collectively referred to as FIG. 1, schematically illustrate in simplified cross-sectional view the operation of an enclosed system that uses focused acoustic radiation to study the interaction between a candidate compound and a bacterial pathogen.

DETAILED DESCRIPTION OF THE INVENTION

Before describing the present invention in detail, it is to be understood that, unless otherwise indicated, this invention is not limited to specific fluids, acoustic devices, substrates, or the like, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise. Thus, for example, the term "a fluid" is intended to mean a single fluid or a mixture of fluids, "a reservoir" is intended to mean one or more reservoirs, "a pathogen" refers to a single pathogen as well as a plurality of pathogens.

In describing and claiming the present invention, the following terminology will be used in accordance with the definitions set out below.

The terms "acoustic coupling" and "acoustically coupled" as used herein refer to a state wherein an object is placed in direct or indirect contact with another object so as to allow acoustic radiation to be transferred between the objects without substantial loss of acoustic energy. When two entities are indirectly acoustically coupled, an "acoustic coupling medium" is needed to provide an intermediary through which acoustic radiation may be transmitted. Thus, an acoustic device may be acoustically coupled to a fluid, such as by immersing the acoustic device in the fluid, or by interposing an acoustic coupling medium between the acoustic device and the fluid, in order to transfer acoustic radiation generated by the acoustic device through the acoustic coupling medium and into the fluid.

The terms "acoustic radiation" and "acoustic energy" are used interchangeably herein and refer to the emission and propagation of energy in the form of sound waves. As with other waveforms, acoustic radiation may be focused using a focusing means, as discussed below.

The term "array" as used herein refers to a two-dimensional arrangement of features, such as an arrangement of reservoirs (e.g., wells in a well plate) or an arrangement of different moieties, including ionic, metallic, or covalent crystalline (e.g., molecular crystalline), composite, ceramic, vitreous, amorphous, fluidic, or molecular materials on a substrate surface (as in an oligonucleotide or peptidic array). Arrays are generally comprised of regular features ordered in, for example, a rectilinear grid, parallel stripes, spirals, and the like, but nonordered arrays may be advantageously used as well. An array is distinguished from the more general term "pattern" in that patterns do not necessarily contain regular and ordered features.

The terms "biomolecule" and "biological molecule" are used interchangeably herein to refer to any organic molecule that is, was, or can be a part of a living organism, regardless of whether the molecule is naturally occurring, recombinantly produced, or chemically synthesized in whole or in part. The terms encompass, for example, monomeric molecules, such as nucleotides, amino acids, and monosaccharides, oligomeric and polymeric species, such as oligonucleotides and polynucleotides, peptidic molecules, such as oligopeptides, polypeptides, and proteins, saccharides, such as disaccharides, oligosaccharides, polysaccharides, mucopolysaccharides, and peptidoglycans (peptido-polysaccharides), and the like. The terms also encompass ribosomes, enzyme cofactors, pharmacologically active agents, and the like. Additional information relating to the term "biomolecule" can be found in U.S. Patent Application Publication No. 20020037579 by Ellson et al.

The teem "enclosure" is used herein in its ordinary sense and refers to anything that encloses. Examples of enclosures include, but are not limited to, bottles, boxes, canisters, cans, cartons, cartridges, containers, drums, jars, and vials.

The term "fluid" as used herein refers to matter that is nonsolid, or at least partially gaseous and/or liquid, but not entirely gaseous. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink," in that ink must contain a colorant and may not be gaseous. Thus, the term "bodily fluid" as used herein refers to any fluid that can be extracted from an individual's body, pathogenic or nonpathogenic. When the individual is a mammal, e.g., human, the term includes fluids such as blood, plasma, serum, interstitial fluid, lymph, bile, spinal fluid, amnionic fluid, urine, saliva, vaginal fluid, and etc.

The term "focusing means" refers to a means for causing waves to converge at a focal point. When acoustic radiation is involved, an "acoustic focusing means" causes acoustic radiation to converge at a focal point either by a device separate from the acoustic energy source that acts like an optical lens, or by the spatial arrangement of acoustic energy sources to effect convergence of acoustic energy at a focal point by constructive and destructive interference. An acoustic focusing means may be as simple as a solid member having a curved surface, or it may include complex structures such as those found in Fresnel lenses, which employ diffraction in order to direct acoustic radiation. Suitable focusing means also include phased array methods as are known in the art and described, for example, in U.S. Pat. No. 5,798,779 to Nakayasu et al. and Amemiya et al. (1997) *Proceedings of the 1997 IS&T NIP13 International Conference on Digital Printing Technologies*, pp. 698-702.

The term "impermeable" is used in its ordinary sense to mean not permitting something to pass through. Similarly, the term "permeable" is used herein in its ordinary sense and means "not impermeable." Typically, the term "impermeable" is used to describe certain enclosures, and the term "permeable" is used to describe certain "substrates" or "surfaces." Thus, a "pathogen-impermeable enclosure" refers to an enclosure that does not allow a pathogen to pass through, and a "permeable substrate" and a "substrate having a permeable surface" refer to a substrate or surface, respectively, that can be permeated with water or other fluid.

The terms "library" and "combinatorial library" are used interchangeably herein to refer to a plurality of chemical or biological moieties arranged in a pattern or an array such that the moieties are individually addressable. In some instances, the plurality of chemical or biological moieties is present on the surface of a substrate, and in other instances, the plurality of moieties represents the contents of a plurality of reservoirs. Preferably, but not necessarily, each moiety is different from each of the other moieties. The moieties may be, for example, peptidic molecules and/or oligonucleotides.

The term "moiety" refers to any particular composition of matter, e.g., a molecular fragment, an intact molecule (including a monomeric molecule, an oligomeric molecule, and a polymer), or a mixture of materials (for example, an alloy or a laminate).

"Optional" or "optionally" means that the subsequently described circumstance may or may not occur, so that the description includes instances where the circumstance occurs and instances where it does not.

The terms "pathogen" and "pathogenic" as used herein refer to any agent that is capable of causing disease and/or a toxic response in an individual. The individual may be a human, an animal (mammalian or otherwise), or on occasion, a plant. Typically, a pathogen referred to herein is a bacterium or virus, but may also be an organic toxin such as strychnine or botulinum, or an inorganic toxin such as arsenic or sodium cyanide. Often, pathogens are biomolecular in nature. Thus, exemplary bacterial pathogens include, but are not limited to, bacteria of the following genera, *Campylobactera, Bacteroides, Bordetella, Haemophilus, Pasteurella, Francisella, Actinobacillus, Klebsiella, Moraxella, Pseudomonas, pneumococci, Proteus, Ornithobacterium, Staphylococci and Streptococci. Salmonella* is another exemplary genus of pathogenic bacteria and includes species such as *Salmonella typhimurium, Salmonella enteriditis,*

*Salmonella gallinarum, Salmonella pullorum, Salmonella arizona, Salmonella heidelberg, Salmonella anatum, Salmonella hadar, Salmonella agana, Salmonella montevideo, Salmonella kentucky, Salmonella infantis, Salmonella schwarzengrund, Salmonella saintpaul, Salmonella brandenburg, Salmonella instanbul, Salmonella cubana, Salmonella bredeney, Salmonella braenderup, Salmonella livingstone, Salmonella berta, Salmonella california, Salmonella senfenberg*, and *Salmonella mbandaka. Mycobacterium* is another type of pathogenic bacteria that is particularly harmful to humans and includes species such as *Mycobacterium tuberculosis, Mycobacterium avium, Mycobacterium paratuberculosis, Mycobacterium bovis* and *Mycobacterium leprae.*

Anaerobic bacterial pathogens include, for example, those in the genera *Peptostreptococci, Actinomyces, Clostridium, Anaerobiospirillum, Fusobacterium*, and *Bilophila*. Thus, exemplary anaerobic bacterial pathogens include, for example, *Peptostreptococci asaccharolyticus, Peptostreptococci magnus, Peptostreptococci micros, Peptostreptococci prevotii, Porphyromonas asaccharolytica, a Porphyromonas canoris, Porphyromonas gingivalis, Porphyromonas macaccae, Actinomyces israelii, Actinomyces odontolyticus, Clostridium innocuum, Clostridium clostridioforme, Clostridium difficile, Bacteroides tectum, Bacteroides ureolyticus, Bacteroides gracilis (Campylobacter gracilis), Prevotella intermedia, Prevotella heparinolytica, Prevotella oris-buccae, Prevotella bivia, Prevotella melaninogenica, Fusobacterium naviforme, Fusobacterium necrophorum, Fusobacterium varium, Fusobacterium ulcerans, Fusobacterium russii*, and *Bilophila wadsworthia.*

Exemplary upper respiratory pathogenic bacteria include, for example, those in the genera *Pseudomonas* and *Legionella*. Thus exemplary upper respiratory upper respiratory pathogens include, *Pseudomonas aeruginosa, Legionella dumoffii, Legionella longbeacheae, Legionella micdadei, Legionella oakridgensis, Legionella feelei, Legionella anisa, Legionella sainthelensi, Legionella bozemanii, Legionella gormanii, Legionella wadsworthii*, and *Legionella jordanis.*

Nonbacterial pathogens include, but are not limited to viruses and fungi and prions. Exemplary viral pathogens include, generally, those of classes I-VI, and more specifically, hepatitis viruses types A-E, ebola viruses, human papilloma viruses, keratoconjunctivitis viruses, Parvoviruses, erythroviruses, dependoviruses, echo viruses, enteroviruses, Epstein-Barr viruses, equine arteritis virus, equine coital exanthema virus, equine encephalosis virus, feline sarcoma viruses, hantaviruses, herpes viruses, human inmmunodeficiency viruses, human T-cell leukaemia viruses, influenza viruses types A-C, JC viruses, Kirsten sarcoma viruses, Lassa viruses, Machupo viruses, Marburg viruses, mastadenoviruses, measles virus, Mengo viruses, Moloney murine leukemia viruses, Newcastle Disease virus, orbiviruses, polio viruses, retroviruses, simian immunodeficiency viruses, small pox viruses, Tamiami viruses, and tobacco mosaic viruses. Fungal pathogens include, for example, *Pyrenophora tritici-repentis, Drechslera sorokiniana, Rhizoctonia cerealis, Fusarium graminearum, Fusarium culmorum, Microdochium nivale, Pseudocercosporella herpotrichoides, Pseudocercosporella herpotrichoides, Septoria nodorum, Septoria tritici, Cladosporium herbarum, Cercospora arachidicola, Helminthosporium sativum, Pyrenophora teres*, and *Pyrenophora tritici-repentis*. It should be noted that these pathogens are enumerated in no particular order and some overlap may occur. Other pathogens are known in the art and identified, for example, in *Sherris Medical Microbiology: An Introduction to Infectious Diseases*, 3rd Ed. (Appleton & Lange, Stamford, Conn., 1994).

Thus, the term "pathogen-containing fluid" refers to non-solid matter that is completely or partially pathogenic in nature. Such a fluid, for example, may be comprised of liquid that contains a pathogen minimally, partially, or fully solvated, dispersed, or suspended therein. Examples of pathogen-containing fluids include, without limitation, a culturing medium containing bacterial or viral infectious agents.

Similarly, the "nonpathogenic" refers to matter that is not pathogenic, i.e., any agent that is not likely to cause disease or a toxic response. Nonpathogenic particles, for example, include, without limitation, beneficial cellular matter such as lactobacilli, yeast, epidermal cells, beads and the like. Nonpathogenic fluids include, for example, sterile saline, glucose solutions, and the like.

The term "radiation" is used in its ordinary sense and refers to emission and propagation of energy in the form of a waveform disturbance traveling through a medium such that energy is transferred from one particle of the medium to another without causing any permanent displacement of the medium itself. Thus, radiation may refer, for example, to electromagnetic waveforms as well as acoustic vibrations.

The term "reservoir" as used herein refers to a receptacle or chamber for containing a fluid. In some instances, a fluid contained in a reservoir necessarily will have a free surface, e.g., a surface that allows acoustic radiation to be reflected therefrom or a surface from which a droplet may be acoustically ejected. A reservoir may also be a locus on a substrate surface within which a fluid is constrained.

The term "substrate" as used herein refers to any item having a surface onto which one or more fluids may be deposited. The substrate may be constructed in any of a number of forms including, for example, wafers, slides, well plates, or membranes. In addition, the substrate may be porous or nonporous as required for deposition of a particular fluid. Suitable substrate materials include, but are not limited to, supports that are typically used for solid phase chemical synthesis, such as polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, and divinylbenzene styrene-based polymers), agarose (e.g., SEPHAROSE®), dextran (e.g., SEPHADEX®), cellulosic polymers and other polysaccharides, silica and silica-based materials, glass (particularly controlled pore glass, or "CPG"), functionalized glasses, and ceramics, as well as such substrates treated with coatings that cover the entirety or a portion of a surface, e.g., treated with microporous polymers (particularly cellulosic polymers such as nitrocellulose), microporous metallic compounds (particularly microporous aluminum), antibody-binding proteins (available from Pierce Chemical Co., Rockford, Ill.), bisphenol A polycarbonate, poly-L-lysine and the like. Such coatings may be deposited via acoustic ejection or other means, to form arrays or other patterns on the substrate surface. Additional information relating to the term "substrate" can be found in U.S. Patent Application Publication No. 20020037579 to Ellson et al.

The invention thus generally relates to methods that employ focused radiation to eject droplets of a fluid from a reservoir and to handle pathogenic materials. Typically, focused acoustic radiation is employed to eject droplets of a pathogenic fluid from a reservoir. In addition, the inventive method may be used in conjunction with a pathogen-impermeable enclosure. For example, the method may involve positioning a substrate so that a designated site on a substrate surface is placed in droplet-receiving relationship with respect to the reservoir. After focused radiation is applied to the fluid in the reservoir such that a droplet of the fluid is deposited at the designated site, the droplet may be sealed in the pathogen-impermeable enclosure.

Figure 1A:
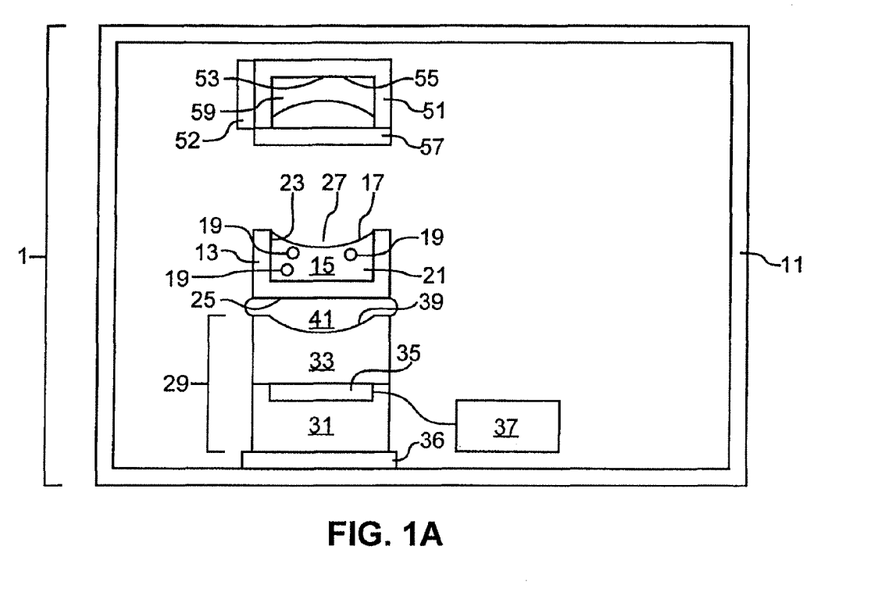
FIG. 1A shows the use of acoustic radiation to locate a pathogenic bacterial particle near the surface of a fluid in a reservoir.
Figure 1B:
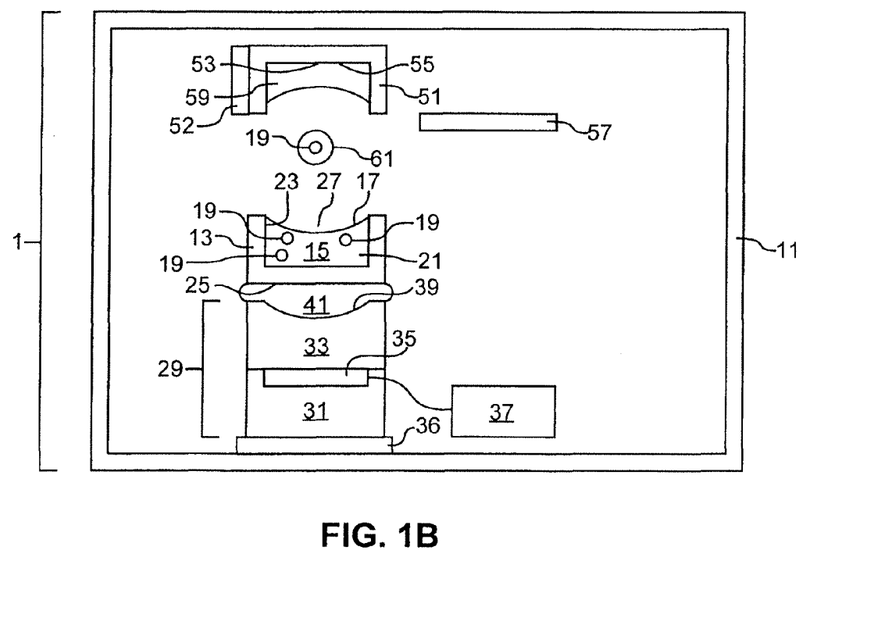
FIG. 1B shows the ejection of a droplet containing a bacterial pathogen from the reservoir onto a designated site of a substrate surface.
Figure 1C:
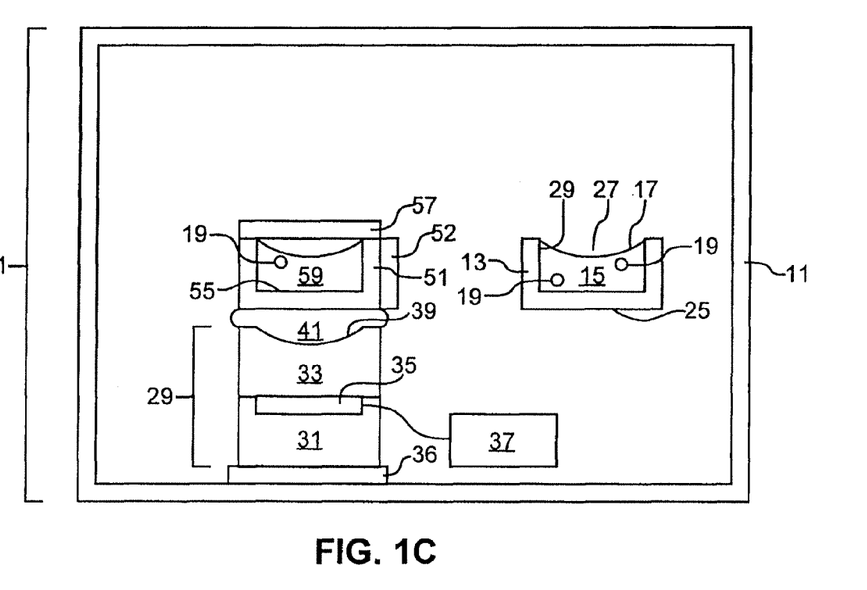
FIG. 1C illustrates the placement of the substrate in acoustically coupled relationship with an acoustic analyzer and an initial acoustic assessment of the pathogenic contents of the well.
Figure 1D:
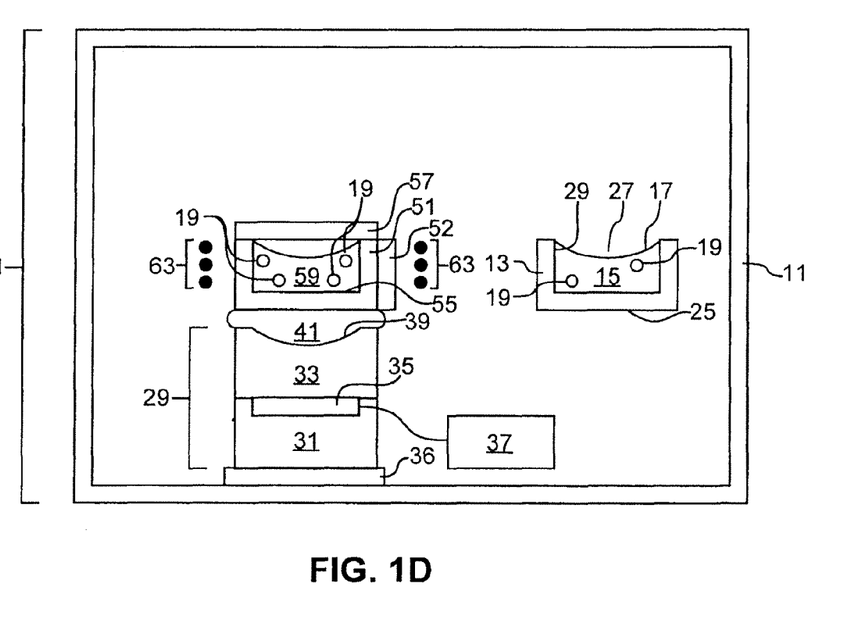
FIG. 1D illustrates a subsequent assessment of the pathogenic contents of the well after exposure to culturing conditions.

The invention also provides a method of monitoring for a change in the amount and/or concentration of a pathogen in a pathogenic fluid. Instead of using focused acoustic radiation to eject droplets from a reservoir, a pathogen-impermeable enclosure is provided enclosing a pathogenic fluid that is comprised of a pathogen and a carrier fluid. Acoustic radiation is then generated to monitor for a change in the amount and/or concentration of the pathogen enclosed in the pathogen-impermeable enclosure. Generally, the invention is suited for use with biological pathogens such as viral and bacterial matter.

FIG. 1 illustrates in simplified cross-sectional view a system for studying the interaction between a candidate compound and a bacterial pathogen. As with all figures referenced herein, in which like parts are referenced by like numerals, FIG. 1 is not to scale, and certain dimensions may be exaggerated for clarity of presentation. The system 1 includes an enclosure 11 that serves to enclose the other components of the system. A reservoir 13 is provided containing a pathogen-containing fluid 15 having a fluid surface 17. The pathogen-containing fluid is comprised of at least one discrete bacterial pathogenic particle 19 suspended in a carrier fluid 21. A plurality of pathogenic particles 19 is depicted in FIG. 1A, though the pathogen-containing fluid may be comprised of a single pathogenic particle as well. As shown, reservoir 13 may be axially symmetric, having a vertical wall 23 extending upward from a circular reservoir base 25 and terminating at an opening 27. The material and thickness of the reservoir base should be such that acoustic radiation may be transmitted therethrough and into the pathogen-containing fluid 15 within the reservoir 13.

The system 1 also includes an acoustic device 29 comprised of an acoustic generator 31 for generating acoustic radiation and a focusing means 33 for focusing the acoustic radiation at a focal point within the fluid from which a droplet is to be ejected near the fluid surface. The acoustic device may be used as an ejector and/or as an analyzer. The acoustic generator contains a transducer, e.g., a piezoelectric element 35, commonly shared by an analyzer. As shown, a combination unit 37 is provided that both serves as a controller and a component of an analyzer. Operating as a controller, the combination unit 37 provides the piezoelectric element 35 with electrical energy that is converted into mechanical and acoustic energy. Operating as a component of an analyzer, the combination unit receives and analyzes electrical signals from the transducer. The electrical signals are produced as a result of the absorption and conversion of mechanical and acoustic energy by the transducer 35.

As shown in FIG. 1, the focusing means 33 may comprise a single solid piece having a concave surface 39 for focusing acoustic radiation, but the focusing means may be constructed in other ways as discussed below. The acoustic device 29 is thus adapted to generate and focus acoustic radiation near a fluid surface 17 when acoustically coupled to a reservoir 13. The acoustic generator 31 and the focusing means 33 may function as a single unit controlled by a single controller, or they may be independently controlled, depending on the desired performance of the device.

There are a number of ways to acoustically couple the acoustic device 29 to the reservoir 13 and thus to the fluid therein. One such approach is through direct contact as is described, for example, in U.S. Pat. No. 4,308,547 to Lovelady et al., wherein a focusing means constructed from a hemispherical crystal having segmented electrodes is submerged in a liquid to be ejected. However, a preferred approach is to acoustically couple the acoustic device to the reservoir 13 and fluid 15 without contacting any portion of the acoustic device, e.g., the focusing means, with the fluid 15. To this end, as illustrated in FIG. 1, the acoustic device is positioned in controlled and repeatable acoustic coupling with fluid 15 in reservoir 13. This typically involves direct or indirect contact between the acoustic device and the external surface of the reservoir 13. When direct contact is used in order to acoustically couple the acoustic device to the reservoir, it is preferred that the direct contact be wholly conformal to ensure efficient acoustic energy transfer. That is, the acoustic device and the reservoir should have corresponding surfaces adapted for mating contact. Thus, if acoustic coupling is achieved between the acoustic device and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of a reservoir having a specially formed inverse surface.

Optimally, acoustic coupling is achieved between the acoustic device and the reservoir through indirect contact, as illustrated in FIG. 1A. In this figure, an acoustic coupling medium 41 is placed between the focusing means 33 and the base 25 of reservoir 13, with the acoustic device and reservoir located at a predetermined distance from each other. The acoustic coupling medium may be an acoustic coupling fluid, preferably an acoustically homogeneous material, in conformal contact with both the acoustic focusing means 33 and each reservoir. In addition, it is important to ensure that the acoustic coupling medium is substantially free of material having different acoustic properties than the fluid medium itself. Furthermore, it is preferred that the acoustic coupling medium be comprised of a material having acoustic properties that facilitate the transmission of acoustic radiation without significant attenuation of acoustic pressure and intensity. Also, the acoustic impedance of the coupling medium should facilitate the transfer of energy from the coupling medium into the container. As shown, the first reservoir 13 is acoustically coupled to the acoustic focusing means 33, such that an acoustic wave is generated by the acoustic generator and directed by the focusing means 37 into the acoustic coupling medium 41, which then transmits the acoustic radiation into the reservoir 13.

Also provided is a substrate 51 having designated site 53 on a surface 55 thereof. As shown, the substrate 51 may be a well that together with a cover 57 form an enclosure adapted to contain a volume of fluid, and the designated site 53 may be located within the interior of the enclosure. A culturing fluid 59 for sustaining and growing bacterial pathogens and, optionally, for containing a candidate compound, may be provided in the interior of the enclosure.

In operation as an analyzer, the acoustic device 33 may first be positioned below reservoir 13, so as to be acoustically coupled to the reservoir through acoustic coupling medium 41. Once the acoustic device and the reservoir are in proper alignment, the transducer 35 of the acoustic generator 31, as depicted in FIG. 1A, is activated to produce acoustic radiation that is directed toward surface 17 of the reservoir, with the amount of energy being insufficient to eject fluid. This is typically accomplished by using an extremely short pulse (on the order of tens of nanoseconds) relative to that required for droplet ejection (on the order of microseconds). The acoustic radiation will then travel in a generally upward direction toward the free fluid surface 17. The acoustic radiation will be reflected under different circumstances. Typically, reflection will occur when there is a change in an acoustic property of the medium through which the acoustic radiation is transmitted. Thus, this first emission of focused acoustic energy permits sonic detection of the presence of a bacterial pathogenic particle sufficiently close to the surface for ejection by virtue of reflection of acoustic energy by the particle. Methods for determining the position of the particles by sonic detection are readily apprehended by those of ordinary skill in the art of acoustic microscopy and related arts. After a pathogenic particle is detected and located, other properties and/or characteristics of the carrier fluid and the pathogenic particle may be measured before the decision to eject is made as described in U.S. patent application Ser. No. 10/010,972, Publication No. 20030101819, entitled "Acoustic Assessment of Fluids in a Plurality of Reservoirs," filed Dec. 4, 2001, by inventors Mutz, Ellson, and Foote.

It will be appreciated by those of ordinary skill in the art that conventional or modified sonar techniques may be employed to locate a pathogenic particle. For example, the acoustic radiation may be reflected back at the piezoelectric element 35, where the acoustic energy will be converted into electrical energy for analysis. Once the analysis has been performed, a decision may be made as to whether and/or how to dispense fluid from the reservoir. If no particle is sufficiently close to the surface for ejection, the acoustic energy may be focused at progressively greater distances from the fluid surface until a pathogenic particle is located and driven closer to the surface by focused acoustic energy or other means. Similarly, the optimum intensity and directionality of the ejection acoustic wave may be determined from similar types of acoustic analysis, optionally in combination with additional data. For example, the desired intensity and directionality of the ejection acoustic wave may be determined by using the data from the above-described assessment relating to reservoir volume or fluid property data, as well as geometric data associated with the reservoir. In addition, the data may show the need to reposition the acoustic device so as to reposition the acoustic generator and/or focusing means with respect to the fluid surface, in order to ensure that the focal point of the ejection acoustic wave is near the fluid surface where desired. Thus, positioning means 36 may be used to ensure that the acoustic device 29 and reservoir 13 are appropriately positioned to carry out acoustic ejection/detection with proper focus.

Thus, one advantage of the invention is the ability to selectively dispense components of the pathogenic fluid. For example, one could select a droplet size too small to entrain a host cell and enable separation of non-cell containing liquid from the pathogenic fluid. There are other methods to accomplish this type of separation including detecting the presence or absence of cells in the ejection zone before opting to dispense the droplet. Such sorting/selective dispensation functionalities are known in the art See, e.g., U.S. Patent Application Publication No. 20020064808 to Mutz et al.; U.S. patent application Ser. No. 09/999,166, Publication No. 20020142286, filed Nov. 29, 2001, for "Focused Acoustic Energy for Ejection Cells from a Fluid," inventors Mutz and Ellson, assigned to Picoliter Inc. (Mountain View, Calif.); U.S. Patent Application Publication No. 20020064809 to Mutz et al.; and U.S. patent application Ser. No. 10/040,926, Publication No. 20020090720, filed Dec. 28, 2001, for "Focused Acoustic Ejection Cell Sorting System and Method," inventors Mutz, Ellson, and Lee, assigned to Picoliter, Inc. (Mountain View Calif.).

In order to deposit droplets of fluid from the reservoir into the well 51, a positioning means 52 is employed to align well 51 with reservoir 13. The cover 57, as depicted in FIG. 1B, is removed from the well 51, and the well 51 is positioned above the reservoir 13 by the positioning means 52 such that the designated site 53 located on the interior surface of the substrate faces the surface 17 of the fluid 15 in the reservoir. Also as shown in FIG. 1B, culturing fluid 59 may be constrained within the well 51 through surface forces. Once a particle that is sufficiently close to the fluid surface 17 of reservoir 13 is located and is determined to meet any other criteria for ejection, the acoustic device 29 serves as an ejector. The acoustic generator 31 is activated to produce an acoustic wave that is focused by the focusing means 33 to eject a volume of fluid that forms droplet 61, which contains a pathogenic particle 19. Generally, an ejected droplet may not contain more than one particle when the droplet to particle volume ratio is less than about 2:1. In some instances, however, a droplet may contain a plurality of pathogenic particles. For example, a single viral particle may have a cross-sectional dimension of about 10 nm. A 1 pL droplet may contain a plurality of viral particles of this size. One way in which the precise amount of energy required to eject only the required volume and no more can be determined by slowly increasing the energy applied, from an amount insufficient to eject a particle desired for ejection, until there is just enough energy applied to eject the droplet the desired distance to the targeted substrate locale. After this initial determination, approximately the same energy, with adjustment for any change in fluid level, may be applied to eject particles of substantially the same volume as the initial calibration particle. As a result, droplet 61 may be ejected from fluid surface 17 into the interior of well 51. As depicted in FIG. 1B, the droplet 61 may contain a single pathogenic particle 19. However, a plurality of pathogenic may be ejected under some instances. In either case, the particle or particles are thus exposed to the candidate compound in culturing fluid 59.

Then, as shown in FIG. 1C, the cover 57 is placed over the well 51 to form an enclosure that contains the ejected pathogenic particle 19 suspended in the culturing fluid 59 with the candidate compound. Typically, the enclosure is sealed such that no matter enters or exits from the enclosure while sealed. The enclosure may then be acoustically coupled to the acoustic device so as to allow acoustic monitoring for changes in the amount and/or concentration of the pathogen enclosed in the enclosure. As depicted, the acoustic device 29 may be positioned below the well 51, in order to achieve acoustic coupling between the acoustic device and the well through the acoustic coupling medium 41. Once the acoustic device and the well are in proper alignment, the transducer 35 of the acoustic generator 31 may be activated to produce acoustic radiation in order to perform an initial assessment of the contents of the well. The assessment may be carried out in a similar manner as set forth herein and in U.S. patent application Ser. No. 10/010,972, Publication No. 20030101819, entitled "Acoustic Assessment of Fluids in a Plurality of Reservoirs," filed Dec. 4, 2001, by inventors Mutz, Ellson, and Foote, and may establish a baseline to which later assessments may be compared. As depicted in FIG. 1D, heating elements 63 within the system enclosure 11 are activated to bring the contents within the well to culturing conditions and the number of pathogenic particles 19 within well 51 are increased. The acoustic assessment may then be carried out at predetermined intervals to determine whether there are any changes in the amount and/or concentration of the pathogen as a result of interaction with the candidate compound. Other forms of assessment, such as optical density, may be used.

It should be apparent that in some embodiments, the invention relates to the use of a pathogen-impermeable enclosure as well as to the ejection of a droplet of pathogenic fluid from a reservoir to a substrate. Accordingly, the invention also provides a device for dispensing one or more droplets of fluid. The device includes a reservoir adapted to contain a fluid, an ejector for applying focused radiation to the reservoir in a manner effective to eject a droplet of fluid from the reservoir, and a means for positioning a substrate such that a substrate is positioned to receive a droplet of fluid from the reservoir. A pathogen-impermeable enclosure is also provided for isolating the reservoir and substrate therein.

Any of a number of different ejectors that apply focused radiation may be used. For instance, the ejector may apply focused electromagnetic radiation of appropriate wavelengths to eject droplets from the reservoir. Typically, the ejector is an acoustic ejector. Although ordinary inkjet technologies involving piezoelectric elements may be employed, it is preferred that the ejector be a nozzleless acoustic device that employs an acoustic generator and a focusing means for focusing the acoustic radiation generated thereby. Exemplary ejectors are described above and in U.S. Patent Application Publication No. 20020037579 to Ellson et al.

The device typically includes a detachable reservoir to provide modularity and interchangeability of components. In addition, the reservoir may be adapted for single use. However, integrated or permanently attached reservoirs may be employed as well. For any of these reservoirs, a pathogen-impermeable cover may be provided for establishing sealing contact therewith.

As alluded to above, the invention may be used for pathogen formatting or reformatting purposes. Thus, a plurality of reservoirs and/or substrates may be provided for use with the present invention. The reservoirs and/or substrates are preferably substantially acoustically indistinguishable from each other. In addition, the reservoirs may be provided in a single-piece unit, such as when the reservoirs represent wells of a well plate. Many well plates suitable for use with the device are commercially available and may contain, for example, 96, 384, 1536, or 3456 wells per well plate. Manufacturers of suitable well plates for use in the employed device include Corning, Inc. (Corning, N.Y.) and Greiner America, Inc. (Lake Mary, Fla.). However, the availability of such commercially produced well plates does not preclude the manufacture and use of custom-made well plates containing at least about 10,000 wells, or as many as 100,000 to 500,000 wells, or more. To facilitate handling of multiple reservoirs, it is preferred that the reservoirs be substantially acoustically indistinguishable from one another. In addition, the reservoirs should be generally arranged in a pattern or an array to provide each reservoir with individual systematic addressability.

The reservoirs or substrates may come into contact with pathogenic fluids, nonpathogenic fluids, or a combination of pathogenic and nonpathogenic fluids. Furthermore, the material used in the construction of reservoirs and substrates should be compatible with the fluids in contact therewith. Thus, if it is intended that the reservoirs or substrates contact an organic solvent such as acetonitrile, polymers that dissolve or swell in acetonitrile would be unsuitable for use in forming the reservoirs or substrates. Similarly, reservoirs or substrates intended to contact DMSO should be compatible with DMSO. Additional information relating to materials selection and construction of reservoirs and substrates, and to fluids with which the reservoirs and substrate may come into contact, are described, for example, in U.S. Patent Application Publication Nos. 20020037579 and 20020037375, each to Ellson et al., and in U.S. Pat. Nos. 5,520,715 and 5,722,479 to Oeftering.

In some instances, a microfluidic device may be used with the invention in place of the substrate and/or reservoir. Microfluidic devices typically have fluid-transporting features of micrometer or submicrometer dimensions in which any number of processes and or analytical techniques involving very small amounts of fluid may be carried out. Microfluidic devices are available from ACLARA BioSciences, Inc. (Mountain View, Calif.), Caliper Technologies Corp. (Mountain View, Calif.), and Fluidigm Corp. (South San Francisco, Calif.). The combined employment of focused acoustic ejection and microfluidic devices is discussed in greater detail in U.S. patent application Ser. No. 10/066,546, Publication No. 20020125424, entitled "Acoustic Sample Introduction for Analysis and/or Processing," filed Jan. 30, 2002, by inventors Ellson and Mutz.

Similarly, the device may further include a means for positioning the acoustic ejector as well as a means for positioning the substrate, such as described, for example, in U.S. Patent Application Publication Nos. 20020037579 and 20020037375, each to Ellson et al. As described in these publications, either or both positioning means may be constructed from, for example, motors, levers, pulleys, gears, a combination thereof, or other electromechanical or mechanical means known to one of ordinary skill in the art. Furthermore, it will be appreciated that various components of the device may require individual control or synchronization. Such control or synchronization may allow for the ejection droplets to prepare an array on a substrate surface.

Furthermore, the device may also include certain performance-enhancing features. For example, the device may include a cooling means for lowering the temperature of the substrate to ensure, for example, that the ejected droplets adhere to the substrate. The cooling means may be adapted to maintain the substrate surface at a temperature that allows fluid to partially, or preferably substantially, solidify after the fluid comes into contact therewith. The device may also include a means for maintaining fluid in the reservoirs at an appropriate temperature, since repeated application of acoustic energy to a fluid will result in heating, which can in turn cause unwanted changes in fluid properties such as viscosity, surface tension, and density. Design and construction of such temperature-maintaining means are known to one of ordinary skill in the art and will involve incorporation of at least one heating element and/or at least one cooling element.

In addition, the device may further include a means for manually manipulating items within the enclosure without compromising the pathogenic impermeability of the enclosure. In addition, a locating means may be provided for locating a discrete particle in the pathogenic fluid. Exemplary locating means are described in U.S. patent application Ser. Nos. 09/727,391, 09/999,166, and 10/033,739 (Publication Nos. 20020064808, 20020142286, and 20020090720 respectively). When the device includes an acoustic generator, the locating means may include an analyzer for analyzing acoustic radiation generated by the acoustic generator. Such an analyzer is typically positioned to receive acoustic radiation generated by the acoustic generator and transmitted through fluid contained in the reservoir. In some instances, as described above, the analyzer is positioned to receive acoustic radiation reflected by a free fluid surface contained in the reservoir. In such a case, the analyzer may include a component common to the acoustic generator, such as a piezoelectric element. Exemplary analyzers are described in U.S. patent application Ser. No. 10/010,972, Publication No. 20030101819, entitled "Acoustic Assessment of Fluids in a Plurality of Reservoirs," filed Dec. 4, 2001, by inventors Mutz, Ellson, and Foote.

Figure 2:
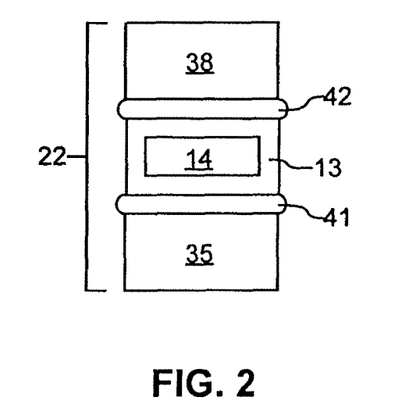
FIG. 2 schematically illustrates in simplified cross-sectional view the acoustic assessment of the pathogenic contents of pathogen-impermeable enclosure in transmissive mode.

It should be noted that acoustic assessment of the pathogenic contents of a pathogen-impermeable enclosure may be performed in transmissive mode rather than in reflective mode. As depicted in FIG. 2, a device 22 may be provided that includes a reservoir 13 adapted to contain a fluid 14. As depicted, the reservoir 13 is in a sealed state. An acoustic radiation generator 35 is positioned below the reservoirs, and analyzer 38 is positioned in opposing relationship with the acoustic radiation generator 35 above the reservoirs. That is, the contents 14 of the reservoir 13 may undergo acoustic assessment when the reservoir 13 is interposed between the acoustic radiation generator 35 and the analyzer 38. The acoustic radiation generator 35 and the analyzer 38 are acoustically coupled to the reservoir via coupling media 41 and 42, respectively. Once the acoustic radiation generator 35, the reservoir 13, and the analyzer 38 are in proper alignment, the acoustic radiation generator 35 is activated to produce acoustic radiation that is transmitted through the reservoir 13 and its contents 14 toward the analyzer 38. The received acoustic radiation is analyzed by analyzer 38.

Thus, the invention also provides a method of monitoring for a change in the amount and/or concentration of a pathogen in a pathogenic fluid. As before, a pathogen-impermeable enclosure is provided that encloses a pathogenic fluid comprising a pathogen and a carrier fluid. The method also involves acoustically monitoring for a change in the amount and/or concentration of the pathogen enclosed in the pathogen-impermeable enclosure.

It should be apparent, then, that the invention permits previously unrealized opportunities in pathogenic studies through the use of focused acoustic radiation. For example, acoustic drop ejection may be used to array and/or rearray infectious pathogenic agents. This may be accomplished, for instance, by using ordinary culturing techniques to grow a stock of bacterial pathogen in a single reservoir that contains culturing media. In some instances, the culturing medium may be provided as a coating on a solid surface. For example, the bacterial pathogen may be immobilized on a substrate surface selected for facile immobilization of cells. Such surfaces include, for example, a collagen-derivatized surface, dextran, polyacrylamide, nylon, polystyrene, and combinations thereof. In some instances, the surfaces are inherently cytophilic. In other instances, a cytophilic substrate surface is provided as a result of surface modification. In a simple embodiment, the culturing medium may be provided as a collagen coating on an interior surface of a well.

Focused radiation may then be used to transfer the culture to the wells of a well plate, wherein each well contains a different antibiotic candidate compound. Then, each well plate may be sealed and put in an incubator for a bacterial growth assay. Every 30 minutes, an acoustic transducer could pass under each well to measure the reflected acoustic energy from a suitable acoustic pulse sent into the well and detecting a change due to the increase in the density of bacterial particles in the plate. In this way, growth rate inhibition for each compound could be determined.

As another example, drug compounds could be arrayed in a series of concentrations, allowing a dose response curve to be constructed. Throughout the process of candidate compound arraying, bacterial regrowth, and growth measurements, the assay plate would remain sealed. As a result, problems such as compound cross-contamination and the danger of exposure of lab personnel to aerosolized pathogens are substantially reduced or eliminated. Since the acoustic frequency content of pulses sent in the wells may be varied, one could distinguish viral particles from bacterial, or bacterial cells from mammalian cells, in situ. Thus, acoustics could be used in the context of an assay where an antibody library displayed on a phage would be used to assess the ability of the antibody to protect mammalian cells from viral infection. The growth of mammalian cells could be readily be distinguished from the growth of bacteria or phage via acoustic detection, since mammalian cells are 10-1000 fold larger than bacterial or viral particles.

Furthermore, the assay system described herein can readily be expanded to the analysis of patient blood samples. Antibody and other tests can be run in the sealed plate format, reducing the chance of exposure of laboratory workers to aerosolized toxins, bacteria, or viruses, while providing a controlled environment for the performance of high-precision diagnostics. In addition, health workers could collect sample specimens and transfer them to microfluidic chips through the use of focused radiation in sealed systems, for use in a laboratory or in fieldwork.

As another example, the invention may be used with a well plate comprised of a plurality of wells each containing a serum sample and a cover or lid that has a substantially planar surface coated with a fluorophore-conjugated antibody. The lid may be then sealed against the well plate. After ejecting droplets from the wells to the coated lid, a homogeneous fluorescence assay may be performed to detect the pathogen which has affinity to the antibody. Since the cover is sealed against the well plate, there is a lowered risk of pathogenic contamination. As a result, the invention provides an improved method for carrying out such assays by reducing the risk of pathogenic exposure.

In some instance, the cover or lid may be patterned with a plurality of different conjugated antibodies bound thereto. Each region of the cover or lid may then be sealed over a well. The antibodies provide multiple fluorescent indicators for droplets of fluid ejected from the well. Based on the spatial position and other aspects of the fluorescent signal, the antibody detection event can be identified.

This flat cover approach provides added advantages when used in conjunction with the invention. For example, it is a relatively simple matter to coat antibodies onto a flat surface. In addition, by using the flat cover, the depth of field for the optics in a fluorescent scanner is reduced. Decoupling the fluorescent read from the well plate is also advantageous. It eliminates the background fluorescence of any materials in the well and issues related to the opacity of the well plate itself to the fluorescent wavelength used for detection. Also, if any well coating is required to promote an environment for amplifying the pathogen, the coating may be applied independently from the application of antibody coating on the cover.

Another advantage of the present invention is that it may be used in applications wherein nucleotidic materials associated with pathogen are employed and/or analyzed. For example, in order to determine whether an individual has been infected with a viral or bacterial pathogen, bodily fluid from the individual may be extracted to determine whether nucleotidic sequences associated with the pathogen is present in the bodily fluid. As such sequences may be present in a small amount, polymerase chain reaction (PCR) may be used in conjunction with the invention.

PCR is a well known technique that makes it possible to start with otherwise undetectable amounts of nucleotidic material such as DNA and create ample amounts of the material for subsequent analysis. In essence, PCR uses a repetitive series of steps to create copies of polynucleotide sequences located between two primer sequences. PCR first involves mixing a template (e.g., target DNA to be amplified), two primer sequences selected so as to be complementary to a portion of the template, PCR buffer, free deoxynucleotide tri-phosphates, such as dATP, dCTP, dGTP, and dTTP, and thermostable DNA polymerase. When a duplex DNA molecule is used as the template, the DNA is denatured, using heat, into two complementary single strands. The primers then anneal to the strands. A subsequent cooling step allows the primers to anneal to complementary sequences on single-stranded DNA molecules containing the sequence to be amplified. Replication of the target sequence is then accomplished by the DNA polymerase which produces a strand of DNA that is complementary to the template. That is, nucleotide monophosphate residues are linked to the primers in the presence of a thermostable DNA polymerase to create a primer extension product. After primer extension, twice as many duplex DNA molecules exist. Repetition of this process doubles the number of copies of the sequence of interest, and multiple cycles increase the number of copies exponentially.

Since PCR requires repeated cycling between higher and lower temperatures, PCR devices must be fabricated from materials capable of withstanding such temperature changes. In some instances, thermocycling may involve a denaturing step at around 90° C. to around 95° C. for 5 to 60 seconds, an annealing step at around 50° C. to around 65° C. for 2 to 80 seconds, and a polymerization step at around 72° C. for 5 to 120 seconds. The sample may be subjected to 30 or more cycles to produce the desired amplification. Thermocycling may be achieved by any suitable and convenient method, e.g., using commercially available thermocyclers, a heating block apparatus, and/or an infrared radiation source in conjunction with cooling devices. After thermocycling is complete, a PCR sample may be cooled to a temperature of around 4° C. for subsequent analysis, processing, treatment or testing. Thus, the materials from which the pathogen-impermeable enclosures of the present invention are made, including for example, any wells, lids, covers, etc. that serve as components of the pathogen-impermeable enclosures, should be mechanically and chemically stable at high temperatures, and capable of withstanding repeated temperature changes without mechanical degradation. Furthermore, the materials should be compatible with the PCR reaction itself, and not inhibit the polymerase or bind DNA. Reactants for the PCR reaction may require encapsulation in a water-impermeable substance such as mineral oil to avoid drying in the thermocycling process.

It should be noted that other nucleic acid amplification and/or reaction techniques are known in the art and that the term "PCR" encompasses such additional techniques as well. That is, the reference to the term "PCR" is intended to include ligase chain reactions, rolling circle amplification, repair chain reactions and other techniques involving reaction mixtures that undergo denaturation, annealing and extension processes.

The assay system as described above may be adapted for use with PCR techniques. For example, in certain PCR based techniques, a sample may be mixed with PCR reagents as well as with a detector for the presence of DNA to quantify the DNA generated by the reaction and/or to determine the presence or identity of a specific pathogen. Accordingly, an exemplary assay involves the ejection of pathogen-containing sample droplets onto a lid, which may then be placed in sealing contact with a well of a well plate to form a pathogen-impermeable enclosure. The ejection may take place either before or after the sample is combined with the PCR reagents. Then, the enclosure is placed in a thermocycler for DNA amplification and for subsequent pathogen identification. The results of the assay can be determined by a variety of methods including the use of the optional DNA quantification material added to the PCR reagent. Methods for selection of primer pairs, both as positive and negative controls for accurate pathogen identification and determination of assay results, are known to those of skill in the art.

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains.

All patents, patent applications, journal articles, and other references cited herein are incorporated by reference in their entireties.

We claim:

1. A method for monitoring for a change in an amount, in a concentration, or in both the amount and the concentration of a pathogen in a pathogenic fluid, comprising:
   (a) acoustically transferring at least one droplet of the pathogenic fluid to a substrate;
   (b) transferring a compound to the substrate;
   (c) sealing the pathogenic fluid and the compound within a pathogen-impermeable enclosure by placing a cover in sealing contact with the substrate;
   (d) performing an initial acoustic assessment of the pathogenic fluid sealed within the pathogen-impermeable enclosure, wherein performing the initial acoustic assessment includes:
      subsequent to step (c), generating, by a piezoelectric acoustic transducer disposed outside of the pathogen-impermeable enclosure, acoustic radiation directed towards the pathogen-impermeable enclosure;
      reflecting the acoustic radiation by the pathogenic fluid;
      receiving, by the piezoelectric acoustic transducer, the acoustic radiation reflected by the pathogenic fluid; and
      analyzing the received acoustic radiation;
   (e) subsequent to step (d), subjecting the pathogen-impermeable enclosure to a process altering the amount, the concentration, or both the amount and the concentration of the pathogen sealed in the pathogen-impermeable enclosure; and
   (f) subsequent to step (e), acoustically monitoring for the change in the amount, in the concentration, or in both the amount and the concentration of the pathogen sealed in the pathogen-impermeable enclosure;
   wherein the acoustically monitoring for the change in the amount, in the concentration, or in both the amount and the concentration of the pathogen sealed in the pathogen-impermeable enclosure includes:
subsequent to step (e), generating, by the piezoelectric acoustic transducer, acoustic radiation directed towards the pathogen-impermeable enclosure;
reflecting the acoustic radiation by the pathogenic fluid;
receiving, by the piezoelectric acoustic transducer, the acoustic radiation reflected by the pathogenic fluid;
analyzing the received acoustic radiation; and
comparing the analyzing of step (d) to the analyzing of step (f).

2. The method of claim 1, wherein the change is an increase in pathogen content.

3. The method of claim 1, wherein the change is a decrease in pathogen content.

4. The method of claim 1, wherein the process of step (e) comprises subjecting the enclosure to a temperature change.

5. The method of claim 4, wherein the process of step (e) comprises raising the temperature of the enclosure.

6. The method of claim 4, wherein the process of step (e) comprises subjecting the enclosure to a temperature selected to facilitate an increase in the amount, in the concentration, or in both the amount and the concentration of the pathogen in the enclosure.

7. The method of claim 4, wherein the process of step (e) comprises subjecting the enclosure to a temperature selected to facilitate a decrease in the amount, in the concentration, or in both the amount and the concentration of the pathogen in the enclosure.

8. The method of claim 2, wherein the increase in pathogen content is responsive to multiplication of the pathogen.

9. The method of claim 3, wherein the decrease in pathogen content is responsive to interaction of the pathogen with the compound.

10. The method of claim 1, wherein the pathogen-impermeable enclosure is formed of polymer.

11. The method of claim 1, wherein the pathogenic fluid comprises a culturing medium.

12. The method of claim 1, wherein the compound is transferred using acoustic radiation.

13. The method of claim 1, wherein the substrate comprises a well of a well plate.

14. The method of claim 1, wherein the compound comprises a nutrient.

15. The method of claim 1, wherein the compound comprises a candidate drug.

16. The method of claim 1, wherein the compound comprises an antibody.

17. The method of claim 1, wherein the pathogenic fluid comprises a blood sample of a patient.

18. The method of claim 1, wherein the compound comprises a drug.

* * * * *